US011540989B2

(12) United States Patent
Tetsu et al.

(10) Patent No.: US 11,540,989 B2
(45) Date of Patent: Jan. 3, 2023

(54) HAIR COSMETIC

(71) Applicant: KAO CORPORATION, Tokyo (JP)

(72) Inventors: Makio Tetsu, Funabashi (JP); Kensuke Aoyagi, Ota-ku (JP); Yuuki Yokota, Kawaguchi (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 16/636,934

(22) PCT Filed: Jul. 10, 2018

(86) PCT No.: PCT/JP2018/026992
§ 371 (c)(1),
(2) Date: Feb. 6, 2020

(87) PCT Pub. No.: WO2019/031176
PCT Pub. Date: Feb. 14, 2019

(65) Prior Publication Data
US 2020/0368130 A1 Nov. 26, 2020

(30) Foreign Application Priority Data

Aug. 10, 2017 (JP) .............................. JP2017-155869

(51) Int. Cl.
| | |
|---|---|
| *A61K 8/41* | (2006.01) |
| *A61K 8/73* | (2006.01) |
| *A61K 8/891* | (2006.01) |
| *A61Q 5/06* | (2006.01) |
| *A61K 8/34* | (2006.01) |
| *A61K 8/368* | (2006.01) |

(52) U.S. Cl.
CPC .............. *A61K 8/416* (2013.01); *A61K 8/342* (2013.01); *A61K 8/345* (2013.01); *A61K 8/347* (2013.01); *A61K 8/368* (2013.01); *A61K 8/738* (2013.01); *A61K 8/891* (2013.01); *A61Q 5/06* (2013.01); *A61K 2800/54* (2013.01)

(58) Field of Classification Search
None
See application file for complete search history.

(56) References Cited

U.S. PATENT DOCUMENTS

| 5,275,761 | A | * | 1/1994 | Bergmann | ............ | A61K 8/345 |
|---|---|---|---|---|---|---|
| | | | | | | 424/70.12 |
| 2007/0110695 | A1 | | 5/2007 | Hoffmann et al. | | |
| 2007/0141007 | A1 | | 7/2007 | Glynn et al. | | |
| 2008/0305056 | A1 | * | 12/2008 | Jenni | ...................... | A61K 8/416 |
| | | | | | | 424/59 |
| 2009/0226381 | A1 | | 9/2009 | Maillefer et al. | | |
| 2011/0165103 | A1 | | 7/2011 | Molenda et al. | | |
| 2011/0174329 | A1 | | 7/2011 | Seng et al. | | |

FOREIGN PATENT DOCUMENTS

| CN | 102448432 | A | | 5/2012 |
|---|---|---|---|---|
| EP | 1 493 424 | A1 | | 1/2005 |
| EP | 102006002767 | | | 7/2007 |
| EP | 2 090 295 | A1 | | 8/2009 |
| EP | 2 196 192 | A1 | | 6/2010 |
| JP | 1-168608 | A | | 7/1989 |
| JP | 5-70327 | A | | 3/1993 |
| JP | H05-85918 | | | 4/1993 |
| JP | 6-506214 | A | | 7/1994 |
| JP | 2000327544 | | * | 11/2000 |
| JP | 2000-344633 | A | | 12/2000 |
| JP | 2003-286137 | A | | 10/2003 |
| JP | 2011-511830 | A | | 4/2011 |
| JP | 2013-87099 | A | | 5/2013 |
| JP | 2014-19817 | A | | 2/2014 |
| JP | 2015-224200 | A | | 12/2015 |
| JP | 2016-121091 | A | | 7/2016 |

OTHER PUBLICATIONS

Merriam Webster, Definition of Rinse, https://www.merriam-webster.com/dictionary/rinse, retrieved online Feb. 3, 2021 (Year: 2021).*
Clearco Products, PSF-2cSt Pure Silicone Fluid Dodecamethylpentasiloxane, http://www.clearcoproducts.com/pdf/volatile/NP-PSF-2cSt.pdf, retrieved online Feb. 3, 2021 (Year: 2021).*
International Search Report dated Oct. 19, 2018 in PCT/JP2018/026992 filed on Jul. 10, 2018, 3 pages.
Database WPI, Week 199316, Thomson Scientific, London, GB; AN 1993-131192, 1993, XP-002785354 (total 1 page).
Roberts et al, "Physical Properties of Low-Molecular Weight Polydimethylsiloxane Fluids", Sandia Report, Feb. 2017, Sandia National Laboratories, Albaquerque, NM & Livermore, CA—54 pages.
Mojsiewicz-Pienkowska , "Size exclusion chromatography with evaporative light scattering detection as a method for speciation analysis of polydimethylsiloxanes. HI. Identification and determination of dimeticone and simeticone in pharmaceutical formulations", Journal_of_Pharmaceutical and Biomedical Analysis, 2012, vol. 58, pp. 200-207.
Sicherheitsdatenblatt_von_der_Fa._Dow Corning Safety Data Sheet, last issue Jun. 4, 2015—11 pages.
Notice of Opposition issued May 18, 2022, in EP patent application 18759432.0—20 pages.

(Continued)

*Primary Examiner* — Jennifer A Berrios
(74) *Attorney, Agent, or Firm* — Oblon, McClelland, Maier & Neustadt, L.L.P.

(57) ABSTRACT

A hair cosmetic containing (A) a specified quaternary ammonium salt, (B) a dimethylpolysiloxane having a weight average molecular weight of 300 or more and 3,000 or less, and water, the hair cosmetic being used by applying on the hair and then rinsing away, wherein the content of the component (B) is 0.5 mass % or more and 60 mass % or less, and a receding contact angle ($\theta_R$) of water droplet as measured by the expansion-contraction method with respect to the surface of a polyethylene plate which is applied with the hair cosmetic and then subjected to water washing is 82° or more and 110° or less. A treatment method of hair including (I) applying the hair cosmetic on the hair and spreading it over the entire hair, and (II) rinsing away the hair cosmetic with water from the entire hair.

14 Claims, No Drawings

(56) References Cited

OTHER PUBLICATIONS

"Shin-Etsu Technical data, Silicone Oil KF-2 Performance Test Results" Shin-Etsu Chemical Co., Ltd., 2014, pp. 1-36 (with English translation).

* cited by examiner

HAIR COSMETIC

FIELD OF THE INVENTION

The present invention relates to a hair cosmetic and a treatment method of hair.

BACKGROUND OF THE INVENTION

Since the moisture contained in the hair wetted with water after shampooing of hair is hardly removed, a lot of persons have a sense such that a drying behavior using a towel, a dryer, or the like is in general troublesome and time consuming. In recent years, requirements for desiring roominess and pleasantness in daily living are becoming strong due to diversification of a lifestyle, and persons who desire to finish simply the drying behavior after shampooing of hair are increasing.

Meanwhile, when the hair is allowed to stand without being thoroughly dried, arrangement of the hairstyle is impaired, thereby causing sleep-mussed hair or untidy hair.

With respect to the aforementioned requirements regarding the hair cosmetic, there are made the following proposals.

JP 2015-224200 A (PTL 1) and JP 2016-121091 A (PTL 2) disclose, as a hair cosmetic which after being applied to the hair, is capable of drying the hair for a short time, a hair cosmetic, such as a hair conditioner composition containing a specified higher alcohol, a cationic surfactant, and a dimethylpolysiloxane.

JP 1-168608 A (PTL 3) discloses a composition for hair drying, containing a volatile silicone, methylphenylpolysiloxane, and ethanol; and JP 2003-286137 A (PTL 4) discloses a cosmetic for hair quick drying, containing a lower alcohol and spherical powdery particles.

JP 2011-511830 A (PTL 5) discloses a hair treatment composition composed of an oil-in-water emulsion composition of a specified amino-modified dimethylpolysiloxane.

SUMMARY OF THE INVENTION

The present invention relates to [1] a hair cosmetic containing (A) a specified quaternary ammonium salt, (B) a dimethylpolysiloxane having a weight average molecular weight of 300 or more and 3,000 or less, and water, the hair cosmetic being used by applying on the hair and then rinsing away, wherein the content of the dimethylpolysiloxane (B) is 0.5 mass % or more and 60 mass % or less, and a receding contact angle (OR) of water droplet as measured by the expansion-contraction method, with respect to the surface of a polyethylene plate which is applied with the hair cosmetic and then subjected to water washing, is 82° or more and 110° or less; and [2] a treatment method of hair including (I) a step of applying the hair cosmetic on the hair and spreading it over the entire hair, and (II) a step of rinsing away the hair cosmetic with water from the entire hair.

DETAILED DESCRIPTION OF THE INVENTION

The above-cited PTLs 1 and 2 are concerned with a type of making the hair bundle wetted with water easy to come apart by a wind of a dryer, thereby shortening the drying time. However, there was room for improvement regarding an effect for time shortening.

In addition, all of the above-cited PTLs 3 to 5 are concerned with a hair treatment composition which is applied on the hair wetted with water and used without rinsing away and are neither a technology from the viewpoint of simplification of a behavior of from shampooing to drying nor shortening of the drying time of hair.

The present invention relates to a hair cosmetic to be used by applying on the shampooed hair and rinsing away, in which before starting a drying behavior of the hair, the moisture remaining among the hairs is naturally drained (dropped) by gravity as far as possible to shorten the drying time of the hair, thereby reducing a load of the drying behavior; and a treatment method of hair.

The present inventors have found that a hair cosmetic containing a specified quaternary ammonium salt and a dimethylpolysiloxane having a specified weight average molecular weight in specified amounts, wherein a receding contact angle ($\theta_R$) of water droplet is controlled to 82° or more to 110° or less is able to solve the aforementioned problem.

Specifically, the present invention relates to the following [1] and [2].

[1] A hair cosmetic containing component (A): at least one component selected from a quaternary ammonium salt (a-1) represented by the following general formula (1) and a quaternary ammonium salt (a-2) represented by the following general formula (2); component (B): a dimethylpolysiloxane having a weight average molecular weight of 300 or more and 3,000 or less; and water, the hair cosmetic being used by applying on the hair and then rinsing away, wherein the content of the component (B) is 0.5 mass % or more and 60 mass % or less; and a receding contact angle ($\theta_R$) of water droplet as measured by the expansion-contraction method, with respect to the surface of a polyethylene plate which is applied with the hair cosmetic and then subjected to water washing, is 82° or more and 110° or less:

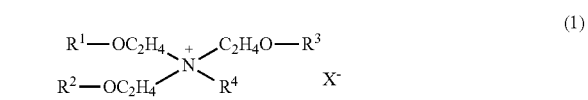

wherein $R^1$, $R^2$, and $R^3$ each independently represent an acyl group having 8 or more and 22 or less carbon atoms or a hydrogen atom, provided that $R^1$, $R^2$, and $R^3$ do not represent a hydrogen atom at the same time; $R^4$ represents an alkyl group having 1 or more and 3 or less carbon atoms; and $X^-$ represents an anion, and

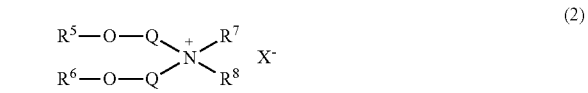

wherein $R^5$ represents an acyl group having 8 or more and 22 or less carbon atoms; $R^6$ represents the aforementioned $R^5$ or a hydrogen atom; $R^7$ and $R^8$ each independently represent an alkyl group having 1 or more and 3 or less carbon atoms; Q represents an ethylene group or a propylene group; and $X^-$ represents an anion.

[2] A treatment method of hair, including the following steps (I) and (II):

(I) a step of applying the hair cosmetic as set forth in the above M on the hair and spreading it over the entire hair, and (II) a step of rinsing away the hair cosmetic with water from the entire hair.

In accordance with the present invention, it is possible to provide a hair cosmetic to be used by applying on the shampooed hair and then rinsing away, in which before starting a drying behavior of the hair, the moisture remaining among the hairs is naturally drained by gravity as far as possible to shorten the drying time of the hair, thereby reducing a load of the drying behavior; and a treatment method of hair.

[Hair Cosmetic]

The hair cosmetic of the present invention is a hair cosmetic containing component (A): at least one component selected from a quaternary ammonium salt (a-1) represented by the foregoing general formula (1) and a quaternary ammonium salt (a-2) represented by the foregoing general formula (2); component (B): a dimethylpolysiloxane having a weight average molecular weight of 300 or more and 3,000 or less; and water, the hair cosmetic being used by applying on the hair and then rinsing away, wherein the content of the component (B) is 0.5 mass % or more and 60 mass % or less; and a receding contact angle ($\theta_R$) of water droplet as measured by the expansion-contraction method with respect to the surface of a polyethylene plate which is applied with the hair cosmetic and then subjected to water washing is 82° or more and 110° or less.

When the hair cosmetic of the present invention is used by applying on the shampooed hair and then rinsing away, before starting a drying behavior of the hair, by naturally draining the moisture remaining among the hairs by gravity as far as possible, it is possible to shorten the drying time of the hair and to reduce a load of the drying behavior. Though the reason for this is not elucidated yet, the following may be considered.

The low-molecular weight (g/mol) dimethylpolysiloxane (B) having a weight average molecular weight of 300 or more and 3,000 or less, which is used in the present invention, readily spreads on the hair surface at the time of applying on the hair because of its low viscosity, and moreover, its ability of repelling water is strong because of its low surface tension. Accordingly, it may be considered that the dimethylpolysiloxane (B) has such an effect for forming a hydrophobic film in water and naturally draining the moisture contained on the hair surface and among the hairs by gravity.

In addition, it may be considered that the quaternary ammonium salt component (A) represented by the general formula (1) or (2) effectively strengthens the operation and effect of the aforementioned low-molecular weight dimethylpolysiloxane (B).

Then, by smoothening the hair cosmetic of the present invention over the hair and then rinsing away it, the aforementioned components (B) and (A) conjointly improve the receding contact angle ($\theta_R$) of water droplet, whereby the moisture remaining on the hair surface and among the hairs after shampooing can be quickly dropped and drained by gravity. Accordingly, the moisture content to be naturally drained from the hair increases, whereby the moisture content remaining on the hair can be significantly reduced. As a result, it may be considered that the hair does not form a bundle but becomes easy to come apart, so that the hair is readily dried.

<Receding Contact Angle ($\theta_R$) of Water Droplet by Expansion-Contraction Method>

In the present invention, the receding contact angle ($\theta_R$) of water droplet is determined by means of dynamic contact angle measurement by the expansion-contraction method. The receding contact angle ($\theta_R$) of water droplet is an index exhibiting drainage properties of the wetted hair bundle.

The dynamic contact angle is known as a change in a dynamic contact angle supposing the state that a water droplet moves on the solid surface by washing, application, or the like. In general, the contact angle on the occasion when the interface of a water droplet advances is defined as an advancing contact angle ($\theta_a$), and the contact angle on the occasion when it recedes is defined as a receding contact angle ($\theta_R$). Details of this definition are described in Kenjiro Meguro and Kunio Esumi ed., *Nure no Kiso to Oyo* (The Elements and Applications of Wetting), (Realize Science & Engineering Center, published in 1989) and Toshio Ishii ed., *Evaluation Technology for Interfacial Phenomena* (published by Technosystem Co., Ltd., pp. 35-37 (2012)).

In the expansion-contraction method, a contact angle when on the occasion of piercing a tip of a needle of a syringe into a water droplet coming into contact with the solid surface and injecting a fixed amount of water, the water droplet advances is defined as the advancing contact angle ($\theta_a$), and a contact angle when on the occasion of sucking water from a water droplet after injecting a fixed amount of water, the water droplet recedes is defined as the receding contact angle ($\theta_R$).

The dynamic contact angle by the expansion-contraction method in the present invention can be, for example, measured at room temperature (25° C.) by using an automatic contact angle meter (DropMaster), manufactured by Kyowa Interface Science Co., Ltd. Specifically, the receding contact angle ($\theta_R$) can be determined by determining an average value of contact angles when ion exchange water is injected at a rate of 6.00 μL/s into a water droplet of ion exchange water in an initial amount of 50 μL for a fixed time and sucked, the measurement is performed at measurement intervals of 100 ms over 1,000 ms, and on the occasion of sucking water from the water droplet, the water droplet recedes. This value is a portion where after starting the suction of water, a fixed value appearing during a time of about 2,000 to 3,000 msec is exhibited.

More specifically, the measurement of the receding contact angle ($\theta_R$) can be performed by the method described in the section of Examples.

In the present invention, the receding contact angle ($\theta_R$) of water droplet as measured by the expansion-contraction method with respect to the surface of a polyethylene plate which is applied with the hair cosmetic and then subjected to water washing is 82° or more and 110° or less.

From the viewpoint of improving the drainage properties of the hair, this receding contact angle ($\theta_R$) is preferably 83° or more, more preferably 85° or more, and still more preferably 87° or more, and it is preferably 108° or less, more preferably 105° or less, and still more preferably 100° or less.

The hair cosmetic having the aforementioned receding contact angle ($\theta_R$) has the following components (A) and (B) and can be obtained by controlling the content of the component (B) to 0.5 mass % or more and 60 mass % or less in the hair cosmetic.

<Component (A)>

The component (A) which is used in the present invention is at least one selected from a quaternary ammonium salt (a-1) represented by the following general formula (1) and a quaternary ammonium salt (a-2) represented by the following general formula (2). Among those, a compound that is the quaternary ammonium salt (a-1) represented by the following general formula (1), in which $R^4$ is a methyl group, is preferred as mentioned later.

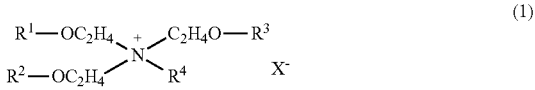

(1)

In the formula, $R^1$, $R^2$, and $R^3$ each independently represent an acyl group having 8 or more and 22 or less carbon atoms or a hydrogen atom, provided that $R^2$, and $R^3$ do not represent a hydrogen atom at the same time; $R^4$ represents an alkyl group having 1 or more and 3 or less carbon atoms; and $X^-$ represents an anion.

(2)

In the formula, $R^5$ represents an acyl group having 8 or more and 22 or less carbon atoms; $R^6$ represents the aforementioned $R^5$ or a hydrogen atom; $R^7$ and $R^8$ each independently represent an alkyl group having 1 or more and 3 or less carbon atoms; Q represents an ethylene group or a propylene group; and $X^-$ represents an anion.

<Component (a-1)>

In the component (A), the component (a-1) is a component composed of a quaternary ammonium salt represented by the following general formula (1). The component (a-1) can be used alone or in combination of two or more of specific compounds included in the general formula (1).

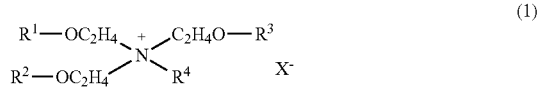

(1)

In the general formula (1), $R^1$, $R^2$, and $R^3$ each independently represent an acyl group having 8 or more and 22 or less carbon atoms (a residue resulting from elimination of an OH group from a fatty acid) or a hydrogen atom, provided that $R^2$, and $R^3$ do not represent a hydrogen atom at the same time; $R^4$ represents an alkyl group having 1 or more and 3 or less carbon atoms; and $X^-$ represents an anion.

The component (a-1) is typically used as a mixture containing plural compounds.

The component (a-1) is preferably a mixture containing compounds represented by the general formula (1), wherein at least one of $R^1$, $R^2$, and $R^3$ is an acyl group. More specifically, the component (a-1) contains a compound (a1) represented by the general formula (1), wherein $R^1$ is an acyl group, and $R^2$ and $R^3$ are each a hydrogen atom; a compound (a2) represented by the general formula (1), wherein $R^1$ and $R^2$ are each an acyl group, and $R^3$ is a hydrogen atom; and a compound (a3) represented by the general formula (1), wherein $R^1$, $R^2$, and $R^3$ are each an acyl group.

In the general formula (1), from the viewpoint of strengthening the operation and effect of the component (B) and the viewpoint of shortening the drying time of the hair, the carbon number of the acyl group represented by $R^1$ to $R^3$ is preferably 10 or more, still more preferably 14 or more, and still more preferably 16 or more, and it is preferably 20 or less, and more preferably 18 or less.

Specific examples of the fatty acid from which the acyl group is derived include one or more selected from saturated fatty acids, such as capric acid (C10), lauric acid (C12), myristic acid (C14), palmitic acid (C16), and stearic acid (C18); unsaturated fatty acids, such as oleic acid (C18), elaidic acid (C18), linoleic acid (C18), and linolenic acid (C18); and fats and oils, such as beef tallow, palm oil, palm kernel oil, coconut oil, sunflower oil, soybean oil, rapeseed oil, safflower oil, cottonseed oil, corn oil, olive oil, hydrogenated palm oil fatty acid, tallow fatty acid, and hydrogenated beef tallow fatty acid.

From the viewpoint of strengthening the operation and effect of the dimethylpolysiloxane (B), $R^4$ in the general formula (1) is preferably a methyl group or an ethyl group, and more preferably a methyl group.

In the general formula (1), examples of $X^-$ that is an anion include organic or inorganic anions. Specific examples of the anion $X^-$ include a halogen ion, an alkyl sulfate ion having 1 or more and 3 or less carbon atoms, an alkyl phosphate ion having 1 or more and 3 or less carbon atoms, a fatty acid ion having 12 or more and 18 or less carbon atoms, and a benzenesulfonate ion which may be substituted with 1 or more and 3 or less alkyl groups having 1 or more and 3 or less carbon atoms. Among those, a halogen ion and an alkyl sulfate ion having 1 or more and 3 or less carbon atoms are preferred; a chlorine atom, a bromine ion, a methyl sulfate ion, and an ethyl sulfate ion are more preferred; and a chlorine ion and a methyl sulfate ion are still more preferred.

<Production of Component (a-1)>

The component (a-1) can be obtained by subjecting an esterification reaction product obtained by a method of subjecting a fatty acid and triethanolamine to a dehydration esterification reaction (hereinafter also referred to as "dehydration esterification method A"), or a method of subjecting a fatty acid lower alkyl ester and triethanolamine to an ester interchange reaction (hereinafter also referred to as "ester interchange method A"), to a quaternization reaction with an alkylating agent. Here, the wording "lower alkyl" refers to an alkyl group having 1 or more and 3 or less carbon atoms and is hereinafter the same.

The fatty acid or fatty acid lower alkyl ester working as a raw material in the dehydration esterification method A or ester interchange method A is preferably a fatty acid composition obtained by saponifying fats and oils selected from beef tallow, palm oil, palm kernel oil, coconut oil, sunflower oil, soybean oil, rapeseed oil, safflower oil, cottonseed oil, corn oil, and olive oil, and from the viewpoint of shortening the drying time of the hair, it is more preferably a fatty acid composition obtained from beef tallow, palm oil, coconut oil, or sunflower oil.

The aforementioned fatty acid or fatty acid lower alkyl ester contains plenty of an alkenyl group having two or more carbon-carbon unsaturated bonds, and therefore, it can be, for example, produced by a crystallization method as described in JP 4-306296 A, a method of subjecting a methyl ester to distillation under reduced pressure as described in JP 6-41578, or a method of performing a selective hydrogenation reaction as described in JP 8-99036 A or the like to control a portion of a fatty acid containing two or more carbon-carbon unsaturated bonds.

(Dehydration Esterification Method A)

In the dehydration esterification method A, it is preferred to perform the reaction while removing condensation water at an esterification reaction temperature of preferably 140° C. or higher, and more preferably 160° C. or higher from the viewpoint of improving the reaction rate, and preferably 230° C. or lower, and more preferably 200° C. or lower from the viewpoint of inhibiting a side reaction. In order to promote the reaction, a known esterification catalyst may be used. For example, a catalyst, such as an inorganic acid, e.g., sulfuric acid or phosphoric acid, an inorganic oxide, e.g., tin oxide or zinc oxide, and an alcoholate, e.g., tetrapropoxytitanium, can be used.

The state of progress of the dehydration esterification reaction can be confirmed through measurement of an acid value (AV) and a saponification value (SV) by the method described in JIS K0070-1992. Preferably, the esterification reaction is terminated by the aforementioned JIS method at the point of time when the acid value reaches 10 mgKOH/g or less, and preferably 6 mgKOH/g or less.

(Esterification Interchange Method A)

In the esterification interchange method A, the reaction is performed while removing a produced lower alcohol at an esterification interchange reaction temperature of preferably 50° C. or higher, and more preferably 100° C. or higher, and preferably 150° C. or lower. In order to promote the reaction, an inorganic alkali, such as sodium hydroxide and potassium hydroxide, or an alkoxy catalyst, such as a methylate and an ethylate, can also be used.

The progress of the reaction is managed by directly quantitating the amount of the unreacted fatty acid lower alkyl ester with a gas chromatograph or the like, and the reaction can be terminated at the point of time when the amount of the unreacted fatty acid lower alkyl ester becomes a predetermined amount or less.

(Quaternization Reaction of Ester Compound)

The above-obtained ester compound is subjected to a quaternization reaction to produce the component (a-1).

Examples of the alkylating agent which is used for the quaternization include methyl halides and dialkyl sulfates. From the viewpoints of reactivity and industrial availability, methyl chloride, dimethyl sulfate, and diethyl sulfate are preferred, and methyl chloride and dimethyl sulfate are more preferred.

In the quaternization reaction, though it is not particularly required to use a solvent, in the case of using a solvent, a lower alcohol, such as ethanol and isopropanol, can be used.

The temperature of the quaternization reaction is preferably 30° C. or higher, and more preferably 40° C. or higher from the viewpoint of improving the reaction rate, and it is preferably 100° C. or lower, and more preferably 80° C. or lower from the viewpoint of inhibiting a side reaction.

The quaternization reaction may be performed at atmospheric pressure (0.1 MPa), or may be performed under pressurized pressure or reduced pressure. From the viewpoint of a load against the facilities, the reaction pressure is preferably 0.09 MPa or more, and more preferably 0.10 MPa or more, and it is preferably 0.5 MPa or less, and more preferably 0.2 MPa or less, in terms of an absolute pressure.

As for a molar ratio of methyl chloride and the ester compound to be used for the quaternization reaction, the methyl chloride can be set to preferably 1 time equivalent or more, and more preferably 1.5 times equivalent or less to 1 equivalent of the amino group of the ester compound.

As for a molar ratio of the dialkyl sulfate and the ester compound to be used for the quaternization reaction, the dialkyl sulfate can be set to preferably 0.9 times equivalent or more, and more preferably 0.95 times equivalent or more, and preferably 1.1 times equivalent or less, and more preferably 0.99 times equivalent or less to 1 equivalent of the amino group of the ester compound.

In order to obtain a mixture in which the compound (a1), the compound (a2), and the compound (a3) in the component (a-1) are satisfied with the aforementioned contents, for example, it is preferred to obtain the mixture of triethanolamine fatty acid esters by performing the reaction in a molar ratio of [(fatty acid or fatty acid lower alkyl ester)/triethanolamine] of preferably 1.3/1 or more, and more preferably 1.5/1 or more, and preferably 2.0/1 or less, and more preferably 1.9/1 or less.

The hair cosmetic of the present invention may contain other reaction product which is produced at the time of production of the component (a-1). For example, though an amine of a fatty acid triester structure and an amine of a fatty acid diester structure may be considered as a non-quaternized unreacted amine, a reaction product containing the amine of a fatty acid triester structure and the amine of a fatty acid diester structure may be contained in a total content of 0 part by mass or more and 30 parts by mass or less based on 100 parts by mass of the component (a-1).

Meanwhile, in view of the fact that an amine of a fatty acid monoester structure is readily quaternized, its content in the reaction product is typically 0.5 parts by mass or less based on 100 parts by mass of the component (a-1). Furthermore, triethanolamine which has not been esterified with a fatty acid and a quaternization product of triethanolamine are contained in a total amount of 0 part by mass or more and 3 parts by mass or less based on 100 parts by mass of the component (a-1), with 90 mass % or more thereof being occupied by the quaternization product.

A degree of quaternization of the component (a-1) is preferably 70% or more, more preferably 80% or more, and still more preferably 90% or more.

In the case of using the reaction product containing the component (a-1), the aforementioned unreacted component or side reaction component may be contained in the hair cosmetic so long as the effects of the present invention are not impaired.

<Component (a-2)>

In the component (A), the component (a-2) is a component composed of a quaternary ammonium salt represented by the following general formula (2). The component (a-2) can be used alone or as a mixture through combination of two or more of specific compounds included in the general formula (2).

(2)

In the general formula (2), $R^5$ represents an acyl group having 8 or more and 22 or less carbon atoms (a residue resulting from elimination of an OH group from a fatty acid); $R^6$ represents the aforementioned $R^5$ or a hydrogen atom; $R^7$ and $R^8$ each independently represent an alkyl group having 1 or more and 3 or less carbon atoms; Q represents an ethylene group or a propylene group; and $X^-$ represents an anion.

The content of a compound (a4) represented by the general formula (2), wherein $R^5$ and $R^6$ are each an acyl group, in the component (a-2) is preferably 60 mass % or more, more preferably 70 mass % or more, and still more preferably 75 mass % or more, and it is preferably 99 mass % or less, more preferably 95 mass % or less, and still more preferably 90 mass % or less.

The content of a compound (a5) represented by the general formula (2), wherein $R^5$ is an acyl group, and $R^6$ is a hydrogen atom, in the component (a-2) is preferably 1 mass % or more, more preferably 5 mass % or more, and still more preferably 10 mass % or more, and it is preferably 40 mass % or less, more preferably 30 mass % or less, and still more preferably 25 mass % or less.

In the general formula (2), the acyl group represented by $R^5$ is preferably a residue resulting from elimination of an OH group from a fatty acid having 12 or more and 20 or less carbon atoms. Specific examples and preferred examples of the acyl group are the same as those in the case of $R^1$ in the general formula (1).

$R^7$ and $R^8$ in the general formula (2) are each preferably a methyl group or an ethyl group; and Q is preferably an ethylene group.

Specific examples and preferred examples of $X^-$ that is an anion are the same as those in the case of the general formula (1).

<Production of Component (a-2)>

The component (a-2) can be obtained by subjecting an esterification reaction product obtained by a method of subjecting a fatty acid and a lower alkyl diethanolamine, in which the alkyl moiety thereof has 1 or more and 3 or less carbon atoms, or a lower alkyl dipropanolamine, in which the alkyl moiety thereof has 1 or more and 3 or less carbon atoms, preferably methyl diethanolamine to a dehydration esterification reaction (hereinafter also referred to as "dehydration esterification method B"), or a method of subjecting a fatty acid lower alkyl ester and a lower alkyl diethanolamine or a lower alkyl dipropanolamine, preferably methyl diethanolamine to an ester interchange reaction (hereinafter also referred to as "ester interchange method B"), to a quaternization reaction with an alkylating agent.

In the reaction for obtaining the esterification production, a molar ratio of the fatty acid or fatty acid lower alkyl ester to the amine is preferably 1.2 or more, more preferably 1.3 or more, and still more preferably 1.4 or more, and it is preferably 1.9 or less, more preferably 1.8 or less, and still more preferably 1.7 or less.

Specific examples and preferred examples of the fatty acid or fatty acid lower alkyl ester are the same as those in the case of the component (a-1).

The preparation of the component (a-2) can be performed in the same manner as in the dehydration esterification method A or ester interchange method A of the component (a-1).

Specific examples and preferred examples of the alkylating agent which is used for the quaternization are the same as those in the component (a-1).

<Dimethylpolysiloxane (B)>

The dimethylpolysiloxane (B) which is used in the present invention is a low-molecular weight dimethylpolysiloxane having a weight average molecular weight of 300 or more and 3,000 or less. This low-molecular weight dimethylpolysiloxane readily spreads on the hair surface because of its low viscosity, and its ability of repelling water is strong because of its low surface tension. Accordingly, the dimethylpolysiloxane (B) has such an effect for improving the natural drainage properties of the moisture remaining on the hair surface and among the hairs.

From the viewpoint of improving the natural drainage properties of the hair, the viewpoint of making the hair after drying with a towel easy to come apart, and the viewpoint of shortening the drying time of the hair, the weight average molecular weight of the dimethylpolysiloxane (B) is preferably 320 or more, more preferably 340 or more, and still more preferably 360 or more, and it is preferably 2,800 or less, more preferably 2,500 or less, still more preferably 2,300 or less, and yet still more preferably 2,000 or less.

In the case of using two or more dimethylpolysiloxanes having a different weight average molecular weight from each other, the weight average molecular weight of the dimethylpolysiloxane (B) means an arithmetic average molecular weight. More specifically, the weight average molecular weight of the dimethylpolysiloxane (B) is preferably 320 or more and 2,800 or less, more preferably 340 or more and 2,500 or less, still more preferably 360 or more and 2,300 or less, and yet still more preferably 360 or more and 2,000 or less.

In the case where two or more dimethylpolysiloxanes are combined and used as the dimethylpolysiloxane (B) having an arithmetic average molecular weight of 300 or more and 3,000 or less, it is preferred that a dimethylpolysiloxane having a weight average molecular weight of 50,000 or more is not used because it hardly spreads on the hair surface at the time of applying on the hair, so that a uniform hydrophobic film is hardly formed in water, and there is a concern that the natural drainage effect of the hair is impaired.

From the viewpoint of improving the natural drainage properties of the hair, the viewpoint of making the hair after drying with a towel easy to come apart, and the viewpoint of shortening the drying time of the hair, the content of the dimethylpolysiloxane having a molecular weight of 300 or more and 2,000 or less in the dimethylpolysiloxane (B) is preferably 50 mass % or more, more preferably 55 mass % or more, still more preferably 75 mass % or more, and yet still more preferably 85 mass % or more, and it is preferably 100 mass % or less.

The weight average molecular weight of the dimethylpolysiloxane (B) and the amount corresponding to the molecular weight of 300 to 2,000 in the dimethylpolysiloxane (B) are a molecular weight expressed in terms of polystyrene as measured by the method described in the section of Examples.

Examples of the dimethylpolysiloxane (B) include at least one selected from a linear dimethylpolysiloxane and a cyclic dimethylpolysiloxane. Among those, a linear dimethylpolysiloxane is more preferred.

Specifically, from the viewpoint of improving the natural drainage properties of the hair, the viewpoint of making the hair after drying with a towel easy to come apart, and the viewpoint of shortening the drying time of the hair, a kinematic viscosity at 25° C. of the linear or cyclic dimethylpolysiloxane is preferably 1.5 mm$^2$/s or more, and more preferably 2 mm$^2$/s or more, and it is preferably 25 mm$^2$/s or less, more preferably 20 mm$^2$/s or less, and still more preferably 15 mm$^2$/s or less.

The measurement of the kinematic viscosity can be performed by the method described in the section of Examples.

Examples of commercially available materials of the linear dimethylpolysiloxane include KF-96 Series, manufactured by Shin-Etsu Chemical Co., Ltd.; SH200C Series and 2-1184 Fluid, manufactured by Dow Corning Toray Co., Ltd.; and Silsoft DML, Element 14 PDMS 5-JC, Element 14 PDMS 10-JC, and Element 14 PDMS 20-JC, manufactured by Momentive Performance Materials Inc.

Examples of the cyclic dimethylpolysiloxane include cyclopentasiloxane and cyclohexanesiloxane. Examples of commercially available materials of the cyclic dimethylpolysiloxane include KF-995, manufactured by Shin-Etsu Chemical Co., Ltd.; SH245 Fluid, DC345 Fluid, and DC246 Fluid, manufactured by Dow Corning Toray Co., Ltd.; and TSF 405, SF 1258, and Silsoft 1217, manufactured by Momentive Performance Materials Inc.

(Content of Each Component in Hair Cosmetic)

From the viewpoint of improving the emulsion dispersion stability of the dimethylpolysiloxane (B) and the viewpoints of allowing the dimethylpolysiloxane (B) to highly remain on the hair, improving the natural drainage properties of the moisture remaining on the hair surface and among the hairs, and enhancing the properties of the hair to come apart, the content of each of the components in the hair cosmetic is as follows.

The content of the component (A) in the hair cosmetic is preferably 0.2 mass % or more, more preferably 0.5 mass % or more, and still more preferably 1 mass % or more, and it is preferably 20 mass % or less, more preferably 15 mass % or less, still more preferably 10% or less, and yet still more preferably 6 mass % or less. Then, the content of the component (A) in the hair cosmetic is preferably 0.2 mass % or more and 20 mass % or less, more preferably 0.5 mass % or more and 15 mass % or less, still more preferably 1 mass % or more and 10 mass % or less, and yet still more preferably 1 mass % or more and 6 mass % or less.

The content of the component (B) in the hair cosmetic is preferably 0.5 mass % or more, preferably 1 mass % or more, still more preferably 3 mass % or more, and yet still more preferably 6 mass % or more, and it is 60 mass % or less, preferably 50 mass % or less, more preferably 40 mass % or less, and still more preferably 20 mass % or less. Then, the content of the component (B) in the hair cosmetic is 0.5 mass % or more and 60 mass % or less, preferably 1 mass % or more and 50 mass % or less, more preferably 3 mass % or more and 40 mass % or less, and still more preferably 6 mass % or more and 20 mass % or less.

The content of water in the hair cosmetic is preferably 30 mass % or more, more preferably 40 mass % or more, still more preferably 50 mass % or more, and yet still more preferably 60 mass % or more, and it is preferably 97 mass % or less, more preferably 95 mass % or less, still more preferably 92 mass % or less, and yet still more preferably 90 mass % or less.

A mass ratio of the component (B) to the component (A) [(B)/(A)] in the hair cosmetic is preferably 0.5 or more, more preferably 1.0 or more, and still more preferably 2 or more from the viewpoints of allowing the dimethylpolysiloxane (B) to highly remain on the hair, effectively hydrophobizing the hair, and improving the natural drainage properties of the hair, the viewpoint of making the hair after drying with a towel easy to come apart, and the viewpoint of shortening the drying time of the hair, and it is preferably 20 or less, more preferably 18 or less, still more preferably 15 or less, and yet still more preferably 5 or less from the viewpoints of stably emulsifying the dimethylpolysiloxane (B) and allowing it to highly remain on the hair. Then, the mass ratio of the component (B) to the component (A) [(B)/(A)] in the hair cosmetic is preferably 0.5 or more and 20 or less, more preferably 1.0 or more and 18 or less, still more preferably 1 or more and 15 or less, and yet still more preferably 1 or more and 5 or less.

(Other Components in Hair Cosmetic and their Contents)

From the viewpoint of improving the smoothness at the time of applying on the hair, the feeling at the time of rinsing, the stability, and so on, in the hair cosmetic of the present invention, an oil component, an aliphatic higher alcohol, a polyhydric alcohol, a silicone other than the dimethylpolysiloxane (B), various polymers exclusive of silicones and proteins, and so on can be further contained. Furthermore, arbitrary components, such as a solubilizing agent, a surfactant, a diluent, a touch improver, a hair repairing agent, a chelating agent, an antioxidant, a humectant, an ultraviolet absorber, a pH adjustor, and a perfume can be suitably added.

The oil component is preferably one that is liquid at room temperature. Specific examples thereof include hydrocarbon oils, such as an α-olefin oligomer, liquid isoparaffin, liquid paraffin, and squalane; triglycerides, such as glyceryl trioctanoate, avocado oil, olive oil, sesame oil, rice-bran oil, safflower oil, soybean oil, corn oil, rapeseed oil, castor oil, cottonseed oil, mink oil, glyceryl tri-2-ethylhexanoate, and caprylic/capric triglyceride; fatty acids, such as oleic acid and isostearic acid; and ester oils, such as isopropyl myristate, butyl myristate, isopropyl palmitate, ethyl oleate, ethyl linoleate, isopropyl linoleate, cetyl caprylate, hexyl laurate, decyl myristate, decyl oleate, oleyl oleate, isostearyl laurate, isotridecyl myristate, isocetyl myristate, isostearyl myristate, octyldodecyl myristate, octyl palmitate, isocetyl palmitate, isostearyl palmitate, propylene glycol dioleate, isodecyl oleate, isopropyl isostearate, cetyl 2-ethylhexanoate, stearyl 2-ethylhexanoate, propylene glycol dicaprylate, and propylene glycol dioleate.

There is a concern that the oil component weakens the effect of the dimethylpolysiloxane (B) and lowers the natural drainage properties of the hair, and therefore, its content is preferably 1 mass % or less, more preferably 0.5 mass % or less, and still more preferably 0.1 mass % or less in the hair cosmetic, and preferably, the oil component is not contained.

Examples of the aliphatic higher alcohol include alcohols having a linear or branched alkyl group or alkenyl group having preferably 8 or more and 26 or less carbon atoms, more preferably 12 or more and 22 or less carbon atoms, and still more preferably 16 or more and 20 or less carbon atoms. Specifically, examples thereof include myristyl alcohol, cetyl alcohol, stearyl alcohol, arachyl alcohol, behenyl alcohol, isostearyl alcohol, 2-octyl dodecanol, oleyl alcohol, and mixtures thereof.

There is a concern that the aliphatic higher alcohol weakens the effect of the component (B) and lowers the natural drainage properties of the hair, and therefore, its content is preferably 10 mass % or less, more preferably 5 mass % or less, still more preferably 3 mass % or less, and yet still more preferably 1 mass % or less in the hair cosmetic, and preferably, the aliphatic higher alcohol is not contained.

From the same viewpoint as that as mentioned above, a mass ratio of the aliphatic higher alcohol to the component (A) [(aliphatic higher alcohol)/(component (A))] is preferably 0.2 or less, more preferably 0.1 or less, and still more preferably 0.05 or less.

Examples of the polyhydric alcohol include ethylene glycol, diethylene glycol, a polyethylene glycol (number average molecular weight: less than 1,000), propylene glycol, dipropylene glycol, a polypropylene glycol (number average molecular weight: less than 1,000), glycerin, diglycerin, a polyglycerin, isoprene glycol, and 1,3-butylene glycol.

There is a concern that the polyhydric alcohol weakens the effect of the dimethylpolysiloxane (B) and lowers the natural drainage properties of the hair, and therefore, its content is preferably 5 mass % or less, more preferably 3 mass % or less, and still more preferably 1 mass % or less in the hair cosmetic, and preferably, the polyhydric alcohol is not contained.

Examples of the various polymers exclusive of silicones and proteins include natural polymers and low-molecular weight polymers resulting from hydrolysis thereof. Furthermore, there are exemplified (i) hydrophobized polymers obtained by subjecting the foregoing polymer to an addition reaction with a hydrophobic group of a fatty acid, an alcohol, or the like; (ii) hydrophilic polymers obtained by adding a hydrophilic group, such as a cation group, an anion group, and an ampholytic group, e.g., betaine, to the foregoing polymer; and (iii) amphipathic polymers obtaining by adding both a hydrophobic group and a hydrophilic group to the foregoing polymer.

Specifically, there are exemplified polysaccharides obtained by subjecting a fatty acid having 16 to 18 carbon atoms to ester bonding; polysaccharides obtained by subjecting a higher alcohol having 1 to 18 carbon atoms to ether bonding; cationized polysaccharides (e.g., cationized cellulose and cationized guar gum); and alkyl cationized polysaccharides (e.g., an alkyl cation-modified cellulose).

Examples of polymers obtained through polymerization of a synthesis system include polymers obtained by performing a reaction of a functional group having an unsaturated bonding group and a cyclic group and then performing polymerization. For example, there are exemplified polymers obtained through a reaction of acrylic acid or a derivative thereof, oxazoline or a derivative thereof, or the like.

There is a concern that such a polymer weakens the effect of the dimethylpolysiloxane (B) and lowers the natural drainage properties of the hair, and therefore, the content of each of the components is preferably 1 mass % or less, more preferably 0.5 mass % or less, still more preferably 0.1 mass % or less, and yet still more preferably 0.05 mass % or less in the hair cosmetic, and preferably, the respective component is not contained.

Examples of the silicone other than the dimethylpolysiloxane (B) include linear polysiloxanes having a weight average molecular weight of more than 3,000, such as dimethylpolysiloxane, methylphenylpolysiloxane, methylhydrogenpolysiloxane, and dimethiconol; modified silicones, such as polyether-modified silicones (e.g., polyoxyethylene (POE)-modified silicones and polyoxypropylene (POP)-modified silicones), polyamino-modified silicones, alcohol-modified silicones (e.g., glycerin-modified silicones), fatty acid-modified silicones, and fluorine-modified silicones; and silicon resins.

The content of the silicone other than the dimethylpolysiloxane (B) is preferably 1 mass % or less, more preferably 0.5 mass % or less, and still more preferably 0.1 mass % or less in the hair cosmetic, and preferably, the silicone other than the dimethylpolysiloxane (B) is not contained.

From the viewpoint of reducing any damage to the hair, or the like, the hair cosmetic of the present invention can contain one or more components selected from an amino acid, a peptide, a protein, an enzyme, gallic acid and a derivative thereof, sterol and a derivative thereof, a plant extract, and a dextrin fatty acid ester. There is a concern that such a component weakens the effect of the dimethylpolysiloxane (B) and lowers the natural drainage properties of the hair, and therefore, the content of each of the components is 1 mass % or less, more preferably 0.5 mass % or less, still more preferably 0.1 mass % or less, and yet still more preferably 0.05 mass % or less in the hair cosmetic, and preferably, the respective component is not contained.

From the viewpoint of enhancing the solubility and dispersibility of various blending components, such as an oil, a polymer, and a plant extract, the hair cosmetic of the present invention can further contain a surfactant other than the component (A). Specifically, the hair cosmetic of the present invention can contain (i) an anionic surfactant, (ii) an ampholytic surfactant, (iii) a nonionic surfactant, or (iv) a cationic surfactant other than the component (A) and the dialkyl cationic surfactant. There is a concern that such a component weakens the effect of the dimethylpolysiloxane (B) due to a relation with other components and lowers the natural drainage properties of the hair, and therefore, the content of each of the components is 1 mass % or less, more preferably 0.5 mass % or less, still more preferably 0.1 mass % or less, and yet still more preferably 0.05 mass % or less in the hair cosmetic, and preferably, the respective component is not contained.

<Production of Hair Cosmetic>

The hair cosmetic of the present invention can be produced in the usual way. For example, purified water, such as ion exchange water, is heated at preferably 50° C. or higher, and more preferably 55° C. or higher, and preferably 95° C. or lower, and more preferably 75° C. or lower and mixed with the component (A) and the component (B), and the mixture is made uniform. Thereafter, if desired, an arbitrary component or components are further added and made uniform, followed by allowing the solution to stand for cooling. As the case may be, an acid or a base is added, and the pH is adjusted, whereby the hair cosmetic of the present invention can be obtained.

(pH)

The pH of the hair cosmetic of the present invention is preferably 2 or more, more preferably 2.5 or more, and still more preferably 3 or more, and it is preferably 6.5 or less, more preferably 5.5 or less, and still more preferably 4.5 or less. The pH of the hair cosmetic is a value at 25° C. when diluted 20 times by mass with water.

(Form, etc. of Hair Cosmetic)

The formulation of the hair cosmetic of the present invention is not particularly limited, and an arbitrary formulation, such as a liquid, a foam, a paste, and a cream, can be taken. The formulation of the hair cosmetic is preferably a liquid, a paste, or a cream, and more preferably a liquid.

As the form of the hair cosmetic of the present invention, there are preferably exemplified those to be used after shampooing within a bathroom, such as a hair rinse, a hair conditioner, a hair treatment, and a hair pack, namely those which after applying on the hair, are applied well smoothly over the hair and then rinsed away. Among those, from the viewpoint of exhibiting the effects of the present invention, it is more preferred to use the hair cosmetic of the present invention as a hair conditioner.

[Treatment Method of Hair]

A treatment method of the hair of the present invention includes the following steps (I) and (II):

(I)$_a$ step of applying the hair cosmetic as set forth in the above [1] on the hair and spreading it over the entire hair, and (II) a step of rinsing away the hair cosmetic with water from the entire hair.

In the step (I), the hair cosmetic of the present invention is first applied on the damp or wetted hair.

At this time, the hair cosmetic may be applied on the hair by hands, or the hair cosmetic may be applied on the hair by using a tool, such as a brush. Preferably, the hair cosmetic is applied on the shampooed hair.

Thereafter, the applied hair cosmetic is spread over the entire hair. In this case, in order to allow the hair cosmetic to penetrate into the interior or surface of the hair, it is preferred to rub into the hair using hands or a tool. Its time is preferably within 10 minutes, and more preferably 30 seconds or more and 5 minutes or less.

Subsequently, in the step (II), the hair cosmetic which has been spread over the entire hair is rinsed away with water. The temperature of the water to be used for rinsing away may be a temperature causing no load on the body, and it is preferably 15° C. or higher and 50° C. or lower, and more preferably 25° C. or higher and 45° C. or lower. The rinsing time is preferably 5 seconds or more and 3 minutes or less.

By the aforementioned steps (I) and (II), at the stage of performing wiping off of the wetted hair after shampooing with a towel and before starting a usual drying behavior for drying with a dryer, the moisture remaining on the hair surface and among the hairs is quickly drained by a gravity, whereby the moisture content of the hair can be significantly reduced. Accordingly, the time of subsequent wiping off of the hair with a towel and drying with a dryer can be shortened, whereby the drying behavior can be reduced.

With respect to the aforementioned embodiments, the present invention further discloses the following hair cosmetics and treatment method of hair.

<1> A hair cosmetic containing component (A): at least one component selected from a quaternary ammonium salt (a-1) represented by the foregoing general formula (1) and a quaternary ammonium salt (a-2) represented by the foregoing general formula (2); component (B): a dimethylpolysiloxane having a weight average molecular weight of 300 or more and 3,000 or less; and water, the hair cosmetic being used by applying on the hair and then rinsing away, wherein the content of the component (B) is 0.5 mass % or more and 60 mass % or less; and a receding contact angle ($\theta_R$) of water droplet as measured by the expansion-contraction method with respect to the surface of a polyethylene plate which is applied with the hair cosmetic and then subjected to water washing is 82° or more and 110° or less.

<2> A hair cosmetic containing component (A): at least one component selected from a quaternary ammonium salt (a-1) represented by the foregoing general formula (1) and a quaternary ammonium salt (a-2) represented by the foregoing general formula (2); component (B): a dimethylpolysiloxane having a weight average molecular weight of 300 or more and 3,000 or less; and water, the hair cosmetic being used by applying on the hair and then rinsing away, wherein the content of a dimethylpolysiloxane having a molecular weight of 300 or more and 2,000 or less in the component (B) is 50 mass % or more and 100 mass % or less;

the content of the component (B) is 0.5 mass % or more and 60 mass % or less; and a receding contact angle ($\theta_R$) of water droplet as measured by the expansion-contraction method with respect to the surface of a polyethylene plate which is applied with the hair cosmetic and then subjected to water washing is 82° or more and 110° or less.

<3> The hair cosmetic as set forth in the above <2>, wherein the content of the dimethylpolysiloxane having a molecular weight of 300 or more and 2,000 or less in the component (B) is 55 mass % or more and 100 mass % or less.

<4> The hair cosmetic as set forth in the above <2>, wherein the content of the dimethylpolysiloxane having a molecular weight of 300 or more and 2,000 or less in the component (B) is 60 mass % or more and 100 mass % or less.

<5> The hair cosmetic as set forth in the above <2>, wherein the content of the dimethylpolysiloxane having a molecular weight of 300 or more and 2,000 or less in the component (B) is 65 mass % or more and 100 mass % or less.

<6> The hair cosmetic as set forth in any of the above <1> to <5>, wherein the component (B) is a straight-chain dimethylpolysiloxane.

<7> The hair cosmetic as set forth in any of the above <1> to <6>, wherein the weight average molecular weight of the component (B) is 320 or more and 2,800 or less.

<8> The hair cosmetic as set forth in any of the above <1> to <6>, wherein the weight average molecular weight of the component (B) is 340 or more and 2,500 or less.

<9> The hair cosmetic as set forth in any of the above <1> to <6>, wherein the weight average molecular weight of the component (B) is 360 or more and 2,300 or less.

<10> The hair cosmetic as set forth in any of the above <1> to <6>, wherein the weight average molecular weight of the component (B) is 360 or more and 2,000 or less.

<11> The hair cosmetic as set forth in any of the above <1> to <10>, wherein the content of the component (A) is 0.2 mass % or more and 20 mass % or less.

<12> The hair cosmetic as set forth in any of the above <1> to <10>, wherein the content of the component (A) is 0.5 mass % or more and 15 mass % or less.

<13> The hair cosmetic as set forth in any of the above <1> to <10>, wherein the content of the component (A) is 1 mass % or more and 10 mass % or less.

<14> The hair cosmetic as set forth in any of the above <1> to <10>, wherein the content of the component (A) is 1 mass % or more and 6 mass % or less.

<15> The hair cosmetic as set forth in any of the above <1> to <14>, wherein the content of the component (B) is 3 mass % or more and 40 mass % or less.

<16> The hair cosmetic as set forth in any of the above <1> to <14>, wherein the content of the component (B) is 6 mass % or more and 20 mass % or less.

<17> The hair cosmetic as set forth in any of the above <1> to <16>, wherein a mass ratio of the component (B) to the component (A) [(B)/(A)] is 0.5 or more and 20 or less.

<18> The hair cosmetic as set forth in any of the above <1> to <16>, wherein a mass ratio of the component (B) to the component (A) [(B)/(A)] is 0.75 or more and 15 or less.

<19> The hair cosmetic as set forth in any of the above <1> to <16>, wherein a mass ratio of the component (B) to the component (A) [(B)/(A)] is 1 or more and 10 or less.

<20> The hair cosmetic as set forth in any of the above <1> to <16>, wherein a mass ratio of the component (B) to the component (A) [(B)/(A)] is 1 or more and 5 or less.

<21> The hair cosmetic as set forth in any of the above <1> to <20>, wherein the content of a silicone other than the component (B) is 1 mass % or less.

<22> The hair cosmetic as set forth in any of the above <1> to <20>, not containing a silicone other than the component (B).

<23> The hair cosmetic as set forth in any of the above <1> to <22>, wherein the content of an oil component is 0.1 mass % or less.

<24> The hair cosmetic as set forth in any of the above <1> to <22>, not containing an oil component.

<25> The hair cosmetic as set forth in any of the above <1> to <24>, wherein the content of an aliphatic higher alcohol is 1 mass % or less.

<26> The hair cosmetic as set forth in any of the above <1> to <24>, not containing an aliphatic higher alcohol.

<27> The hair cosmetic as set forth in any of the above <1> to <26>, wherein the content of a polyhydric alcohol is 1 mass % or less.

<28> The hair cosmetic as set forth in any of the above <1> to <26>, not containing a polyhydric alcohol.

<29> The hair cosmetic as set forth in any of the above <1> to <28>, wherein the content of various polymers exclusive of silicones and proteins is 0.5 mass % or less.

<30> The hair cosmetic as set forth in any of the above <1> to <28>, wherein the content of various polymers exclusive of silicones and proteins is 0.05 mass % or less.

<31> The hair cosmetic as set forth in any of the above <1> to <28>, not containing various polymers exclusive of silicones and proteins.

<32> The hair cosmetic as set forth in any of the above <1> to <31>, wherein the content of one or more components selected from an amino acid, a peptide, a protein, and an enzyme is 0.5 mass % or less.
<33> The hair cosmetic as set forth in any of the above <1> to <31>, wherein the content of one or more components selected from an amino acid, a peptide, a protein, and an enzyme is 0.05 mass % or less.
<34> The hair cosmetic as set forth in any of the above <1> to <31>, not containing one or more components selected from an amino acid, a peptide, a protein, and an enzyme.
<35> The hair cosmetic as set forth in any of the above <1> to <31>, wherein the content of one or more components selected from gallic acid and a derivative thereof, sterol and a derivative thereof, a plant extract, and a dextrin fatty acid ester is 0.5 mass % or less.
<36> The hair cosmetic as set forth in any of the above <1> to <31>, wherein the content of one or more components selected from gallic acid and a derivative thereof, sterol and a derivative thereof, a plant extract, and a dextrin fatty acid ester is 0.05 mass % or less.
<37> The hair cosmetic as set forth in any of the above <1> to <31>, not containing one or more components selected from gallic acid and a derivative thereof, sterol and a derivative thereof, a plant extract, and a dextrin fatty acid ester.
<38> The hair cosmetic as set forth in any of the above <1> to <37>, wherein the content of a surfactant other than the component (A) is 0.5 mass % or less.
<39> The hair cosmetic as set forth in any of the above <1> to <37>, wherein the content of a surfactant other than the component (A) is 0.1 mass % or less.
<40> The hair cosmetic as set forth in any of the above <1> to <37>, not containing a surfactant other than the component (A).
<41> Use as the hair cosmetic as set forth in any of the above <1> to <40>.
<42> Use of the hair cosmetic as set forth in any of the above <1> to <40> as a hair conditioner.
<43> A treatment method of hair, including the following steps (I) and (II):
   (I) a step of applying the hair cosmetic as set forth in any of the above <1> to <40> on the hair and spreading it over the entire hair, and
   (II) a step of rinsing away the hair cosmetic with water from the entire hair.

EXAMPLES (1) Measurement of Weight Average Molecular Weight (Mw) of Dimethylpolysiloxane The weight average molecular weight (Mw) of the dimethylpolysiloxane was measured by means of gel permeation chromatography (GPC).

The Mw was calculated by using a column having two mixed gel columns (Shodex K-804L, manufactured by Showa Denko K.K.) connected with each other as a column, using chloroform (one for high-performance liquid chromatography, manufactured by Kanto Chemical Co., Inc.) as a mobile phase and a diluent solvent, using a differential refractive index ($R^1$) detector as a detector, and using a monodisperse polystyrene having an already-known molecular weight as a standard substance.

The amount corresponding to the molecular weight of 300 to 2,000 in the dimethylpolysiloxane was determined from an integral molecular weight distribution curve.

(2) Measurement of Kinematic Viscosity of Dimethylpolysiloxane

The kinematic viscosity of the dimethylpolysiloxane was measured at 25° C. by using an Ubbelohde viscometer on the basis of JIS Z8803: "Methods for viscosity measurement of liquid".

(3) Measurement of Receding Contact Angle ($\theta_R$)
(i) Preparation of Substrate for Measurement:

A polyethylene plate (500 mm×500 mm×1 mm, a product number: 6-619-01, manufactured by AS ONE Corporation) was chopped in a size of about 2 cm in square to prepare a test piece; a 50-time diluted aqueous solution of an RBS-50 solution (manufactured by Sigma-Aldrich Co. LLC) was used as a washing liquid; and the test piece was dipped in the washing liquid and stirred, and then evenly flooded, followed by allowing to stand at 25° C. overnight. Thereafter, the washing liquid was rinsed away with ion exchange water, and the resulting test piece was allowed to stand for drying under conditions at 25° C.

The above-obtained test piece was dipped in a hair cosmetic sample for 2 seconds and then taken out into air at 25° C., and the surface of the test piece was subjected to water washing, specifically, rinse-washing with ion exchange water for 2 seconds. After rinse-washing, the drained-off test piece was immediately measured as a substrate for measurement with respect to the receding contact angle.

(ii) Measurement of Receding Contact Angle ($\theta_R$):

Using an automatic contact angle meter, DM-501 Hi (manufactured by Kyowa Interface Science Co., Ltd.), the receding contact angle of a water droplet generated on the aforementioned substrate for measurement was measured at 25° C. by the expansion-contraction method.

Ion exchange water was used for the measurement. The amount of the ion exchange water at the initial time was set to 50 μL, ion exchange water was injected into this liquid droplet and sucked, and the receding contact angle at the time of suction was measured. The amount of injection and suction of the water exchange was set to 6.00 μL/s, and after the injection time reached 4,700 msec, the suction was immediately started and performed for 4,700 msec.

The measurement of the receding contact angle was performed in the following manner. That is, after completion of the injection of water, the suction of the water droplet was started; at the stage when an end part (contact line) of the water droplet started to recede by the suction of the ion exchange water, the measurement was performed at measurement intervals of 100 ms over 1,000 ms or so; and on the occasion of sucking water from the water droplet, an average value of contact angles when the water droplet receded was determined, thereby determining the receding contact angle ($\theta_R$). This value is a portion where after starting the suction of water, a fixed value appearing during a time of about 2,000 to 3,000 msec is exhibited.

Production Example 1 [Production of Quaternary Ammonium (a-1a) Represented by the General Formula (1)]

(1) In a one-liter reaction vessel, triethanolamine (1.0 mol, Triethanolamine-S, manufactured by Nippon Shokubai Co., Ltd.), a semi-hydrogenated palm oil fatty acid (1.65 mol, Palmac 605T, manufactured by Acidchem Inc), and 0.28 g of BHT were charged, followed by purging with nitrogen. Subsequently, the pressure was reduced from atmospheric pressure to 13.3 kPa at 170° C. over 1 hour while bubbling nitrogen, and an esterification reaction was performed for 7 hours, thereby obtaining 569 g of a triethanolamine ester having an acid value of 2.0 mgKOH/g.

512 g (0.9 mol) of the obtained triethanolamine ester and 0.7 g of BHT were mixed, and 107.8 g (0.855 mol) of dimethyl sulfate was dropped at atmospheric pressure and 45 to 65° C. in a nitrogen atmosphere over 2 hours. After aging at 60 to 65° C. for 1.5 hours, 84.9 g of ethanol was added such that the solvent amount in the quaternary ammonium salt was finally 12 mass %, and the contents were mixed at 55 to 65° C. for 0.5 hours, thereby obtaining a quaternary ammonium salt (a-1a).

(2) The quaternary ammonium salt obtained in the above (1) was analyzed by the high-performance liquid chromatography (HPLC) method and quantitated with tetraoctylammonium bromide as an internal standard substance. As a result, the reaction product contained 88 mass % of the component (a-1a) and 12 mass % of ethanol.

Production Example 2 [Production of Quaternary Ammonium (a-1b) Represented by the General Formula (1)]

A fatty acid (mass ratio of oleic acid/linoleic acid/linolenic acid/stearic acid/palmitic acid=80/10/2/2/6) and triethanolamine were subjected to an esterification reaction in a reaction molar ratio (fatty acid/triethanolamine) of 1.87/1, thereby obtaining an esterification reaction product containing an amine compound that is a precursor of the quaternary ammonium salt represented by the general formula (1).

As for the fatty acid composition of the raw material, the fatty acid was subjected to composition analysis by means of gas chromatography, and an area % of each fatty acid was considered to be mass % and calculated.

1 mass % of the unreacted fatty acid was contained in the above-obtained esterification reaction product. A quaternization reaction was performed with dimethyl sulfate such that the amount of the methyl group was 0.96 equivalents to the amine of the amine compound in the esterification reaction product, and ethanol was then added.

The obtained reaction product was subject to analysis of a composition ratio of the respective components by the HPLC method. As a result, the reaction product contained 85 mass % of the component (a-1b) and 15 mass % of ethanol.

Examples 1 to 7 and Comparative Examples 1 to 8

In a wide-mouthed standard bottle (PS-No. 6, manufactured by Tokyo Glass Kikai Co., Ltd.), all of respective raw materials (inclusive of water) as shown in Table 1 were added to make 35 g in a total amount, and the bottle was then stoppered. The contents were heated and mixed in a warm water bath at 65° C. for about one hour. At the point of time when the raw materials were thoroughly mixed, the bottle was taken out from the warm water bath and shaken by hands until the mixture was uniformly emulsified and dispersed through visual inspection. Thereafter, the resultant was allowed to stand for cooling in an environment at 25° C., thereby obtaining a hair conditioner composition whose temperature became 25° C.

The obtained hair conditioner was used and measured for the receding contact angle ($\theta_R$), and then evaluated for "easiness of hair to come apart" and "degree of natural drainage of hair (%)" in the following methods.

The results are shown in Table 1 along with the data before the treatment with the hair conditioner.

Details of the respective components in Table 1 are as follows.

<Component (A)>
  Dicocoylethyl hydroxyethylmonium methosulfate: DEHYQUART L80T, manufactured by BASF SE This compound is a quaternary ammonium salt represented by the general formula (1), wherein $R^1$ and $R^2$ are each an acyl group; $R^3$ is a hydrogen atom; $R^4$ is a methyl group; and $X^-$ is a methyl sulfate ion.

<Component (B)>
*1 to 6 are a dimethylpolysiloxane (DMPS), manufactured by Shin-Etsu Chemical Co., Ltd.
*1: KF-96A (Mw: 260, kinematic viscosity: 1 mm²/s at 25° C.)
*2: KF-96L (Mw: 392, kinematic viscosity: 2 mm²/s at 25° C.)
*3: KF-96A (Mw: 1,290, kinematic viscosity: 10 mm²/s at 25° C.)
*4: KF-96A (Mw: 2,230, kinematic viscosity: 20 mm²/s at 25° C.)
*5: KF-96A (Mw: 5,130, kinematic viscosity: 50 mm²/s at 25° C.)
*6: KF-96A (Mw: 8,870, kinematic viscosity: 100 mm²/s at 25° C.)
*7: SH245 Fluid, cyclopentasiloxane manufactured by Dow Corning Toray Co., Ltd., Mw: 371, kinematic viscosity: 4 mm²/s at 25° C.

<Evaluation Methods>
(1) Easiness of Hair to Come Apart after Drying with Towel:

A hair bundle of an Asian straight hair with no chemical treatment history (hair length: about 20 cm, dry weight: 9 g) was washed with warm tap water by using a plain shampoo and then thoroughly rinsed away. 3 g of the sample liquid was applied on the hair bundle in a wetted state after shampooing and thoroughly applied smoothly over the entire hair. The applied sample liquid was then rinsed away with warm tap water for 5 seconds, and the hair bundle was then squeezed with fingers and drained off until water droplets did not drop. The treated hair bundle was placed on a pan balance, and the hair bundle was impregnated with tap water such that the content of water became 9 g that is equal to the dry weight (9 g) of the hair bundle (18 g in total).

On a double-folded paper towel of 40 cm×16 cm in square (a product name: Ellieair® Pro-Wipe Soft Towel White, manufactured by Daio Paper Corporation, dry weight: about 10 g) placed on an acrylic plate of 32 cm×16 cm (thickness: 4 mm, weight: 293 g), the aforementioned hair bundle having been impregnated with water was laid such that the hair bundle was not bent; the same paper towel of 40 cm×16 cm in square was placed thereon; the assembly was sandwiched by an acrylic plate of 32 cm×16 cm (thickness: 4 mm, weight: 293 g); and a metallic weight (850 g) was then placed thereon, followed by performing towel pressing for 2 minutes.

Thereafter, the root of the water-absorbed hair bundle was held and swung three times at an amplitude of about 30°, and the fineness (easiness to come apart) of the hair bundle was graded with the following three scores by means of organoleptic evaluation by three expert panelists and evaluated in terms of a total score of the three persons (perfect score: 9).

Score 3: Any portion of the hair bundle considerably finely comes apart.
Score 2: Though fine bundles exist, thick bundles partially remain.
Score 1: Fine bundles do not substantially exist, and thick bundles remain in the majority.

When the total score is 8 or more, a significant difference in the "easiness of hair to come apart" can be sufficiently recognized.

(2) Degree of natural drainage of hair (%):

A hair bundle of an Asian straight hair with no chemical treatment history (hair length: about 20 cm, dry weight: 9 g) was washed with warm tap water by using a plain shampoo having the following blending formulation and then thoroughly rinsed away. 3 g of the hair cosmetic sample was applied on the hair bundle in a wetted state after shampooing and thoroughly applied smoothly over the entire hair. The applied sample liquid was then rinsed away with warm tap water for 5 seconds, and the hair bundle was then squeezed with fingers and drained off until water droplets did not drop. The treated hair bundle was placed on a pan balance, and the hair bundle was impregnated with tap water such that the content of water became 9 g that is equal to the dry weight (9 g) of the hair bundle (18 g in total). Thereafter, the hair bundle was suspended on the vertical line of the pan balance such that the hair ends were positioned at about 5 cm above the pan, and the weight (drainage amount) of the dripped water droplet was measured with a lapse of time.

The drainage amount after three minutes of suspension was weighed, and the degree of natural drainage of hair (%) was calculated according to the following equation.

Degree of natural drainage of hair (%)=[(Drainage amount (g) after three minutes of suspension)/(Water content (g) of hair bundle before suspension)]×100

[(Water content (g) of hair bundle before suspension) =(Dry weight (g) of hair)]

When the degree of natural drainage (%) is 50% or more, shortening of the drying time can be recognized.

[Blending Formulation of Plain Shampoo (pH: 7.0)]

| | |
|---|---|
| 25% Polyoxyethylene (2.5) lauryl ether sulfuric acid sodium salt: | 62.0 mass % |
| Lauric acid diethanolamide: | 2.3 mass % |
| Disodium edetate: | 0.15 mass % |
| Sodium benzoate: | 0.5 mass % |
| Sodium chloride: | 0.8 mass % |
| 75% Phosphoric acid: | Proper amount |
| Perfume, methylparaben: | Minute amount |
| Purified water: | Balance |
| Total | 100 mass % |

TABLE 1

| | | | Example | | | | | | | Comparative Example | |
|---|---|---|---|---|---|---|---|---|---|---|---|
| | | | 1 | 2 | 3 | 4 | 5 | 6 | 7 | 1 | 2 |
| Blend composition of hair cosmetic (mass %) | Component (A) | Quaternary ammonium salt by Production Example 1 (active ingredient: 88%) | 4 | | | 4 | 4 | 4 | 4 | 4 | |
| | | Quaternary ammonium salt by Production Example 2 (active ingredient: 85%) | | 4 | | | | | | | 4 |
| | | Dicocoylethyl hydroxyethylmonium methosulfate (active ingredient: 80%) | | | 4 | | | | | | |
| | Component (B) | DMPS of Mw of 260 (1 mm$^2$/s) *1 | | | | | | | | | |
| | | DMPS of Mw of 392 (2 mm$^2$/s) *2 | 8 | 8 | 8 | | | | 40 | | |
| | | DMPS of Mw of 1,290 (10 mm$^2$/s) *3 | | | | | 6.7 | | | | |
| | | DMPS of Mw of 2,230 (20 mm$^2$/s) *4 | | | | 8 | | | | | |
| | | DMPS of Mw of 5,130 (50 mm$^2$/s) *5 | | | | | | | | | |
| | | DMPS of Mw of 8,870 (100 mm$^2$/s) *6 | | | | | 1.3 | | | | |
| | | Cyclopentasiloxane of Mw of 371 *7 | | | | | | 8 | | | |
| | Ion exchange water | | Balance | Balance | Balance | Balance | Balance | Balance | Balance | Balance | Balance |
| | | Total | 100 | 100 | 100 | 100 | 100 | 100 | 100 | 100 | 100 |
| | | Content of component (A) (mass %) | 3.5 | 3.4 | 3.2 | 3.5 | 3.5 | 3.5 | 3.5 | 3.5 | 3.4 |
| | | Mass ratio [component (B)/component (A)] | 2.3 | 2.4 | 2.5 | 2.3 | 2.3 | 2.3 | 11.4 | — | — |
| | | Mw of dimethylpolysiloxane (DMPS) *8 | 392 | 392 | 392 | 2230 | 2520 | 371 | 392 | — | — |
| | | Content of DMPS of Mw of 300 to 2,000 (mass %) *9 | 92 | 92 | 92 | 55 | 72 | 100 | 92 | — | — |
| Evaluation | | Receding contact angle ($\theta_R$) (°) | 93 | 98 | 91 | 88 | 83 | 93 | 83 | 78 | 74 |
| | | Easiness of hair to come apart after drying with towel | 9 | 8 | 9 | 8 | 8 | 9 | 9 | 6 | 5 |
| | | Degree of natural drainage of hair (%) | 55 | 55 | 53 | 50 | 50 | 55 | 54 | 49 | 49 |

TABLE 1-continued

|  |  |  | Comparative Example 3 | 4 | 5 | 6 | 7 | 8 | Before treatment |
|---|---|---|---|---|---|---|---|---|---|
| Blend composition of hair cosmetic (mass %) | Component (A) | Quaternary ammonium salt by Production Example 1 (active ingredient: 88%) |  | 4 | 4 | 4 | 4 | 4 |  |
|  |  | Quaternary ammonium salt by Production Example 2 (active ingredient: 85%) |  |  |  |  |  |  |  |
|  |  | Dicocoylethyl hydroxyethylmonium methosulfate (active ingredient: 80%) | 4 |  |  |  |  |  |  |
|  | Component (B) | DMPS of Mw of 260 (1 mm²/s) *1 |  |  |  |  | 8 |  |  |
|  |  | DMPS of Mw of 392 (2 mm²/s) *2 |  | 0.4 | 80 |  |  |  |  |
|  |  | DMPS of Mw of 1,290 (10 mm²/s) *3 |  |  |  |  |  |  |  |
|  |  | DMPS of Mw of 2,230 (20 mm²/s) *4 |  |  |  |  |  |  |  |
|  |  | DMPS of Mw of 5,130 (50 mm²/s) *5 |  |  |  | 8 |  |  |  |
|  |  | DMPS of Mw of 8,870 (100 mm²/s) *6 |  |  |  |  |  | 8 |  |
|  |  | Cyclopentasiloxane of Mw of 371 *7 |  |  |  |  |  |  |  |
|  | Ion exchange water |  | Balance | Balance | Balance | Balance | Balance | Balance | 100 |
|  | Total |  | 100 | 100 | 100 | 100 | 100 | 100 | 100 |
|  | Content of component (A) (mass %) |  | 3.2 | 3.5 | 3.5 | 3.5 | 3.5 | 3.5 | — |
|  | Mass ratio [component (B)/component (A)] |  | — | 0.1 | 22.7 | 2.3 | 2.3 | 2.3 | — |
|  | Mw of dimethylpolysiloxane (DMPS) *8 |  | — | 392 | 392 | 5130 | 260 | 8870 | — |
|  | Content of DMPS of Mw of 300 to 2,000 (mass %) *9 |  | — | 92 | 92 | 15 | 12 | 4 | — |
| Evaluation | Receding contact angle ($\theta_R$) (°) |  | 61 | 76 | *10 | 78 | 74 | 76 | 81 |
|  | Easiness of hair to come apart after drying with towel |  | 6 | 7 | *10 | 3 | 7 | 3 | 4 |
|  | Degree of natural drainage of hair (%) |  | 48 | 49 | *10 | 49 | 49 | 44 | 44 |

*1: to 6: KF-96, manufactured by Shin-Etsu Chemical Co., Ltd.
*7: SH245 Fluid, Dow Corning Tray Co., Ltd.
*8: Example 5 is an arithmetic average molecular weight.
*9: Content of dimethylpolysiloxane of Mw of 300 to 2,000 in the component (B)
*10: Impossible for measurement due to separation of component It is noted from Table 1 that the hair cosmetics of Examples 1 to 7 are large in the receding contact angle ($\theta_R$) of water droplet and excellent in the easiness of the hair to come apart after drying with a towel and the degree of natural drainage of hair, as compared with the hair cosmetics of Comparative Examples 1 to 8.

INDUSTRIAL APPLICABILITY

In accordance with the hair cosmetic of the present invention, when used by applying on the shampooed hair and rinsing away, before starting a drying behavior of the hair, the moisture remaining among the hairs is naturally drained by gravity as far as possible, thereby making it possible to shorten the drying time of the hair and to reduce a load of the drying behavior.

The invention claimed is:
1. A hair cosmetic, comprising:
component (A): a quaternary ammonium salt (a-1) represented by the formula (1);
component (B): a dimethylpolysiloxane having a weight average molecular weight of from 320 to 2,800 g/mol, wherein the dimethylpolysiloxane comprises from 85 mass % to 100 mass % of a dimethylpolysiloxane having the molecular weight of from 300 to 2,000 g/mol; and
water,
wherein a content of the component (B) is from 6 mass % to 40 mass %;
a mass ratio of the component (B) to the component (A) [(B)/(A)] is from 2.0 to 11.4; and
a receding contact angle ($\theta_R$) of water droplet as measured by the expansion-contraction method, with respect to the surface of a polyethylene plate which is applied with the hair cosmetic and then subjected to water washing, is from 82° to 110°:

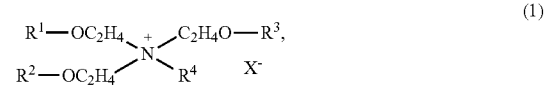
(1)

wherein $R^1$, $R^2$, and $R^3$ each independently represent an acyl group having 8 to 22 carbon atoms or a hydrogen atom, provided that $R^1$, $R^2$, and $R^3$ do not represent a hydrogen atom at the same time; $R^4$ represents an alkyl group having 1 to 3 carbon atoms; and $X^-$ represents an anion.

2. The hair cosmetic according to claim 1, wherein the component (A) is the quaternary ammonium salt (a-1) represented by the formula (1), wherein $R^4$ is a methyl group.

3. The hair cosmetic according to claim 1, wherein a content of the component (A) is from 0.2 mass % to 20 mass %.

4. The hair cosmetic according to claim 1, wherein the dimethylpolysiloxane is a linear dimethylpolysiloxane.

5. A hair conditioner, comprising:
the hair cosmetic according to claim 1, wherein the hair conditioner is in the form of a liquid, a paste, or a cream.

6. A method of treating hair, comprising:
(I) applying the hair cosmetic according to claim 1 on the hair and spreading it over the entire hair; and
(II) rinsing away the hair cosmetic with water from the entire hair.

7. The hair cosmetic according to claim 1, wherein the hair cosmetic further comprises 1 mass % or less of a silicone other than the dimethylpolysiloxane component (B).

8. The hair cosmetic according to claim 1, wherein the hair cosmetic further comprises 1 mass % or less of an oil component.

9. The hair cosmetic according to claim 1, wherein the hair cosmetic further comprises 1 mass % or less of an aliphatic alcohol, wherein the aliphatic alcohol comprises an alkyl group or alkenyl group having 8 to 26 carbon atoms.

10. The hair cosmetic according to claim 1, wherein the hair cosmetic further comprises 1 mass % or less of a polyhydric alcohol.

11. The hair cosmetic according to claim 1, wherein the hair cosmetic further comprises 0.5 mass % or less of a surfactant other than the component (A).

12. The hair cosmetic according to claim 1, wherein the hair cosmetic further comprises 0.5 mass % or less of a polymer other than a silicone and a protein.

13. The hair cosmetic according to claim 1, wherein the hair cosmetic further comprises 0.5 mass % or less of at least one component selected from the group consisting of an amino acid, a peptide, a protein, and an enzyme.

14. The hair cosmetic according to claim 1, wherein the hair cosmetic further comprises 0.5 mass % or less of at least one component selected from the group consisting of gallic acid and a derivative thereof, sterol and a derivative thereof, a plant extract, and a dextrin fatty acid ester.

* * * * *